United States Patent
Shank et al.

(10) Patent No.: US 9,265,596 B2
(45) Date of Patent: Feb. 23, 2016

(54) ANCHORS WITH OPEN HEADS

(75) Inventors: Peter Shank, Boyleston, MA (US); David A. Melanson, Hudson, NH (US); Barry Maxwell, Spencer, MA (US); Sean K. Holmes, West Roxbury, MA (US); James Loper, Wales, MA (US); Ian K. Parker, Bristol, RI (US); Andy H. Levine, Newton, MA (US)

(73) Assignee: GI Dynamics, Inc., Lexington, MA (US)

( * ) Notice: Subject to any disclaimer, the term of this patent is extended or adjusted under 35 U.S.C. 154(b) by 0 days.

(21) Appl. No.: 13/394,975

(22) PCT Filed: Sep. 10, 2010

(86) PCT No.: PCT/US2010/048444
§ 371 (c)(1),
(2), (4) Date: Mar. 8, 2012

(87) PCT Pub. No.: WO2011/031981
PCT Pub. Date: Mar. 17, 2011

(65) Prior Publication Data
US 2012/0179086 A1     Jul. 12, 2012

Related U.S. Application Data

(60) Provisional application No. 61/361,806, filed on Jul. 6, 2010, provisional application No. 61/276,381, filed on Sep. 11, 2009.

(51) Int. Cl.
*A61M 5/00* (2006.01)
*A61F 2/04* (2013.01)
(Continued)

(52) U.S. Cl.
CPC ............. *A61F 2/04* (2013.01); *A61F 5/0076* (2013.01); *A61F 2/2409* (2013.01); *A61F 2/848* (2013.01);
(Continued)

(58) Field of Classification Search
CPC ......... A61F 2/2409; A61F 2/04; A61F 2/848; A61F 5/0076; A61F 5/0089; A61F 2220/0008; A61F 2220/0016; A61F 2230/0091
USPC ................ 604/8; 623/1.11, 1.23, 23.65
See application file for complete search history.

(56) References Cited

U.S. PATENT DOCUMENTS 4,258,724 A   3/1981  Balat et al.
4,616,439 A   10/1986 Lee
(Continued)

FOREIGN PATENT DOCUMENTS

DE      10125999 A1   11/2002
EP      0 701 800 A1   3/1996
(Continued)

OTHER PUBLICATIONS

International Preliminary Report on Patentability, Date of Mailing: Jan. 17, 2013 for International Application No. PCT/US2011/042334 filed Jun. 29, 2011.
(Continued)

*Primary Examiner* — Tatyana Zalukaeva
*Assistant Examiner* — Andrew J Mensh
(74) *Attorney, Agent, or Firm* — Hamilton, Brook, Smith & Reynolds P.C.

(57) ABSTRACT

An implant (100) includes a protrusion (110) with an open or rounded loop (112) (or open head) connected to a collapsible anchor. The protrusion may include a straight length of wire (114) or a helical length wire, with one or more wire loops (112) at the end of the length forming the loop. Upon deployment within the gastrointestinal tract, the protrusion expands from a collapsed state, alongside the anchor, to a relaxed state, in which the protrusion extends outward from the anchor. As the protrusion expands to its relaxed state, it pushes the loop into the wall of the duodenum, causing the loop to penetrate the duodenal wall. A pocket of scar tissue forms about the head and possibly through an opening in the head, securing the anchor within the duodenum. The implant may also include a thin-walled sleeve that is coupled to the anchor and extended from the anchor into the intestine.

36 Claims, 10 Drawing Sheets

(51) Int. Cl.
*A61F 5/00* (2006.01)
*A61F 2/06* (2013.01)
*A61F 2/24* (2006.01)
*A61F 2/848* (2013.01)

(52) U.S. Cl.
CPC ......... *A61F 5/0089* (2013.01); *A61F 2002/045* (2013.01); *A61F 2002/8483* (2013.01); *A61F 2220/0008* (2013.01); *A61F 2220/0016* (2013.01); *A61F 2230/0091* (2013.01); *A61F 2250/0031* (2013.01)

(56) References Cited

U.S. PATENT DOCUMENTS

| | | |
|---|---|---|
| 5,531,783 A | 7/1996 | Giele et al. |
| 5,630,829 A | 5/1997 | Lauterjung |
| 5,942,276 A | 8/1999 | Chivers et al. |
| 6,558,429 B2 | 5/2003 | Taylor |
| 6,663,633 B1 | 12/2003 | Pierson |
| 6,695,875 B2 | 2/2004 | Stelter et al. |
| 6,730,056 B1 | 5/2004 | Ghaem et al. |
| 7,025,791 B2 | 4/2006 | Levine et al. |
| 7,081,132 B2 | 7/2006 | Cook et al. |
| 7,101,395 B2* | 9/2006 | Tremulis et al. ............ 623/2.11 |
| 7,122,058 B2 | 10/2006 | Levine et al. |
| 7,160,312 B2 | 1/2007 | Saadat |
| 7,267,694 B2 | 9/2007 | Levine et al. |
| 7,329,285 B2 | 2/2008 | Levine et al. |
| 7,338,520 B2 | 3/2008 | Bailey et al. |
| 7,351,258 B2 | 4/2008 | Ricotta et al. |
| 7,476,256 B2 | 1/2009 | Meade et al. |
| 7,608,114 B2 | 10/2009 | Levine et al. |
| 7,678,068 B2 | 3/2010 | Levine et al. |
| 7,758,535 B2 | 7/2010 | Levine et al. |
| 7,771,382 B2 | 8/2010 | Levine et al. |
| 7,780,701 B1 | 8/2010 | Meridew et al. |
| 7,815,589 B2 | 10/2010 | Meade et al. |
| 7,819,836 B2 | 10/2010 | Levine et al. |
| 7,837,643 B2 | 11/2010 | Levine et al. |
| 7,914,568 B2 | 3/2011 | Cully et al. |
| 8,029,455 B2 | 10/2011 | Stack et al. |
| 8,057,420 B2 | 11/2011 | Meade et al. |
| 8,834,553 B2 | 9/2014 | Melanson et al. |
| 2003/0144578 A1 | 7/2003 | Koster, Jr. |
| 2004/0215324 A1* | 10/2004 | Vonderwalde et al. ....... 623/1.15 |
| 2004/0220682 A1* | 11/2004 | Levine et al. ............ 623/23.65 |
| 2005/0085923 A1 | 4/2005 | Levine et al. |
| 2005/0102024 A1* | 5/2005 | Riccotta et al. ............. 623/1.23 |
| 2005/0125020 A1 | 6/2005 | Meade et al. |
| 2005/0143691 A1 | 6/2005 | Picha et al. |
| 2005/0154448 A1 | 7/2005 | Cully et al. |
| 2005/0240259 A1 | 10/2005 | Sisken et al. |
| 2006/0009858 A1 | 1/2006 | Levine et al. |
| 2006/0161139 A1 | 7/2006 | Levine et al. |
| 2006/0212042 A1 | 9/2006 | Lamport et al. |
| 2007/0083258 A1 | 4/2007 | Falotico et al. |
| 2007/0270944 A1* | 11/2007 | Bergheim et al. ............ 623/2.18 |
| 2008/0071383 A1 | 3/2008 | Levine et al. |
| 2008/0097466 A1 | 4/2008 | Levine et al. |
| 2008/0161922 A1 | 7/2008 | Rhoda |
| 2008/0195226 A1 | 8/2008 | Williams et al. |
| 2008/0221673 A1 | 9/2008 | Bobo et al. |
| 2008/0234834 A1* | 9/2008 | Meade et al. ............. 623/23.65 |
| 2009/0012541 A1 | 1/2009 | Dahl et al. |
| 2009/0082847 A1 | 3/2009 | Zacharias et al. |
| 2009/0149871 A9 | 6/2009 | Kagan et al. |
| 2009/0177215 A1 | 7/2009 | Stack et al. |
| 2009/0254174 A1 | 10/2009 | Case et al. |
| 2009/0259306 A1 | 10/2009 | Rowe |
| 2009/0264985 A1 | 10/2009 | Bruszewski |
| 2009/0270966 A1 | 10/2009 | Douk et al. |
| 2009/0306763 A1 | 12/2009 | Roeder et al. |
| 2010/0305590 A1 | 12/2010 | Holmes et al. |
| 2011/0040318 A1 | 2/2011 | Marco et al. |
| 2011/0276091 A1 | 11/2011 | Melanson et al. |
| 2014/0358063 A1 | 12/2014 | Melanson et al. |

FOREIGN PATENT DOCUMENTS

| | | |
|---|---|---|
| JP | 2005-021504 | 1/2005 |
| WO | WO 99/49792 A1 | 10/1999 |
| WO | WO 00/18322 A1 | 4/2000 |
| WO | WO 03/024355 A1 | 3/2003 |
| WO | WO 03/057090 A1 | 7/2003 |
| WO | WO 2004/041133 A1 | 5/2004 |
| WO | WO 2004/087014 A2 | 10/2004 |
| WO | WO 2006/002492 A1 | 1/2006 |
| WO | WO 2007/025028 A1 | 3/2007 |
| WO | WO 2007/038786 A1 | 4/2007 |
| WO | WO 2007/079413 A2 | 7/2007 |
| WO | WO 2007/136735 A2 | 11/2007 |
| WO | WO 2008/048973 A2 | 4/2008 |
| WO | WO 2009/029744 A1 | 3/2009 |
| WO | WO 2009/052188 A1 | 4/2009 |
| WO | WO 2009/129079 A1 | 10/2009 |
| WO | WO 2010/126889 A1 | 11/2010 |
| WO | WO 2011/031981 A1 | 3/2011 |
| WO | WO 2012/006146 A1 | 1/2012 |

OTHER PUBLICATIONS

International Preliminary Report on Patentability mailed Mar. 22, 2012, for International Application No. PCT/US2010/048444 filed Sep. 10, 2010.
U.S. Appl. No. 14/459,612, filed Aug. 14, 2014.
International Search Report and the Written Opinion of the International Searching Authority mailed on Nov. 12, 2010 for International Application No. PCT/US2010/048444 filed on Sep. 10, 2010.
International Search Report and the Written Opinion of the International Searching Authority mailed Sep. 28, 2011 of International Application No. PCT/US2011/042334 filed Jun. 29, 2011.

* cited by examiner

ANCHORS WITH OPEN HEADS

RELATED APPLICATIONS

This application is the U.S. National Stage of International Application No. PCT/US2010/048444, filed Sep. 10, 2010, which designates the U.S., published in English, and claims the benefit of U.S. Provisional Application Nos. 61/361,806 filed Jul. 6, 2010, and 61/276,381 filed Sep. 11, 2009. The entire teachings of the above applications are incorporated herein by reference.

BACKGROUND

Obesity is associated with a wide variety of health problems, including Type 2 diabetes, hypertension, coronary artery disease, hypercholesteremia, sleep apnea, and pulmonary hypertension. It also exerts an enormous strain on the body that affects the organs, the nervous system, and the circulatory systems. Obesity rates have been rising for years in the United States, causing corresponding increases in healthcare expenditures.

Curing obesity has so far vexed the best efforts of medical science. Dieting is not an adequate long-term solution for most obese people, especially those with a body-mass index of over 30. Stomach stapling, or gastroplasty, reduces the size of the stomach, leading to reduced appetite and weight loss, but eventually the stomach stretches and the patient's appetite returns to pre-surgery levels. Roux-en-Y gastric bypass reduces the size of the stomach and the length of the intestine, and leads to both weight loss and alleviation of the Type 2 diabetes common to obese patients. Although gastric bypass appears to provide a more permanent solution than gastroplasty, complication rates associated with gastric bypass are between 2% and 6%, with mortality rates of about 0.5-1.5%.

Endoscopically delivered gastrointestinal implants, such as those described in commonly assigned U.S. Pat. Nos. 7,025,791 and 7,608,114 to Levine et al., incorporated herein by reference in their entireties, provide the benefits of gastric bypass without the hazards of surgery. For example, an implant may include a thin-walled, floppy sleeve that is secured in the stomach or intestine with a collapsible anchor. The sleeve extends into the intestine and channels partially digested food, or chyme, from the stomach through the intestine in a manner that may cause weight loss and improve diabetes symptoms. The sleeve and anchor can be removed endoscopically when treatment is over or if the patient desires.

SUMMARY

Embodiments of the present invention provide improved anchoring of an implant in the gastrointestinal tract and can increase the duration that an implant can be anchored in the intestine by encouraging stable tissue reactions to the implant. An implant according to principles of the present invention may include a long protrusion with an open loop connected to a collapsible anchor. The collapsible anchor, which may, for example, be a wave anchor or a stent comprising a network of struts, is configured to be deployed within a lumen in a mammalian body. Upon deployment, the collapsible anchor expands within the lumen, and the protrusion expands away from the anchor, pushing the open loop against the wall of the lumen. Over time, the protrusion and the open loop penetrate the luminal wall, and the open loop may project through the far side of the luminal wall. A pocket of scar tissue forms about the open loop and through an opening in the open loop, securing the anchor within the lumen. The implant may have additional protrusions, each of which is connected to the anchor and includes an open loop. Each additional open loop also includes an opening and is adapted to penetrate the luminal wall upon deployment of the collapsible anchor.

Each open loop may have an inner opening with a width of between about 1 mm and about 13 mm, or, more preferably, an inner diameter of about 3 mm. Typically, the protrusion extends along a total length of between about 6 mm and about 13 mm from the collapsible anchor upon full deployment from the collapsible anchor. The protrusion and the open loop may be formed of wire (e.g., nitinol wire) with a preferred diameter of about 0.010 inch to about 0.040 inch, and more preferably about 0.020 inch.

The open loop can be formed of a loop of wire, and the protrusion can be formed of a straight length of wire extending from the loop of wire. The open loop may be oriented in a variety of directions with respect to the collapsible anchor. For example, the open loop may define a plane that is perpendicular to the lumen wall when the protrusion is deployed. Alternatively, the open loop may define a plane that is parallel to the lumen wall when the protrusion is deployed. When the protrusion is in a collapsed state, it folds against or along the side of the collapsible anchor. When relaxed, straight protrusions typically extend outwards from the collapsible anchor at an angle of between about 45 degrees and about 135 degrees, or, more preferably, to an angle of about 80 degrees or about 90 degrees. At these angles, the expanded straight protrusion pushes the loop outward, causing an edge of the loop to engage the luminal wall.

Alternatively, the protrusion can include a length of wire formed in a helix. The wire used to form the helix may be coiled to form the loop, which can be oriented such that it is parallel to the luminal wall when deployed within the lumen. (Other orientations of the loop are also possible.) The helix may have a tapered profile (e.g., a conical profile) when viewed from the side, and can be flattened alongside the collapsible anchor. The collapsed implant can be inserted into the lumen endoscopically. Releasing the helix and the anchor from the collapsed state causes the helix to push the loop away from the anchor, which, in turn, causes a face of the loop to engage the luminal wall. The implant may also include an end effect at or near the tip of the loop to aid penetration of the loop through the luminal wall.

The implant can be collapsed, for removal from the lumen, with an optional drawstring that runs through the opening in the loop or through additional retaining hooks or loops connected to the loop or the protrusion. Pulling on the drawstring collapses the loop and protrusion towards the collapsible anchor, and away from the luminal wall. Collapsing an implanted helix may cause coils in the helix to shear fibrotic tissue formed about the helix depending on the spacing and orientation of the coils that make up the helix.

An implant with a protrusion and an open loop can also include an unsupported, thin-walled sleeve coupled to the collapsible anchor and configured to extend into the lumen (e.g., the intestine) upon deployment of the collapsible anchor. The implant may also include a restrictor plate instead of or in addition to the thin-walled sleeve.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF PREFERRED EMBODIMENTS

Figure 1A:
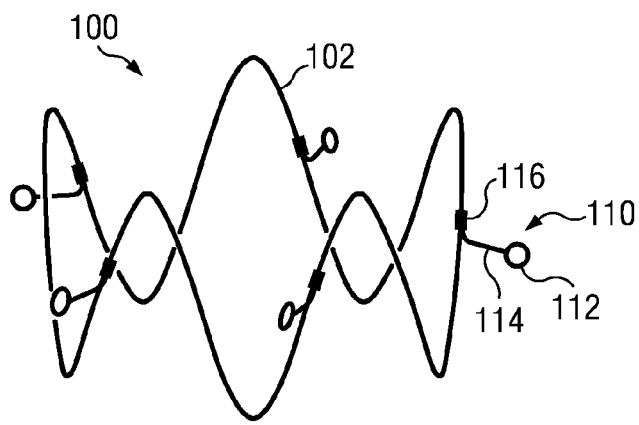
FIGS. 1A-1D are perspective, plan, and elevation views of straight protrusions with open loop s coupled to a wave anchor.

A description of example embodiments of the invention follows. An anchor may be used to secure a sleeve in the intestine of a patient for treating obesity and/or type-2 diabetes as described in commonly assigned U.S. Pat. Nos. 7,025, 791; 7,608,114; 7,476,256; U.S. patent application Ser. No. 10/858,852, filed on Jun. 1, 2004, by Levine et al.; U.S. patent application Ser. No. 11/330,705, filed on Jan. 11, 2006, by Levine et al.; U.S. patent application Ser. No. 11/827,674 filed on Jul. 12, 2007, by Levine et al., all of which are incorporated herein by reference in their entireties.

As described in the above-referenced patents and patent applications, straight, sharp barbs fixed to a self-expanding anchor may be used to secure an implant to the duodenal wall. However, the body's healing response stimulates a progressive tissue proliferation around sharp barbs in response to the injury caused as the anchor pushes the sharp barbs into the wall of the duodenum. The inflammatory response to the injury produces a mix of granulation and more stable fibrous tissue (i.e., scar tissue). This causes thickening of the duodenal wall over time resulting in barbs disengaging from the tissue. As sharp barbs separate from the duodenal wall, the implant may become unstable and migrate or rotate within the duodenum.

Long barbs tend be better than short barbs at holding implants securely for longer periods. Without subscribing to any particular theory, it appears that longer barbs are more stable because it takes more time for the inflammatory thickening to separate longer barbs from the muscle layer. However, there is a practical limit to how long sharp barbs can be because longer sharp barbs are more likely to infiltrate surrounding organs. Very long sharp barbs can pierce through the muscle wall of the intestine and into adjacent structures and could potentially cause leaks, bleeding, or adhesions to other organs.

Protrusions with open loops (also called open heads), on the other hand, can secure an implant for longer periods of time while minimizing the risk of damage to nearby organs. In one embodiment, the protrusion, which is relatively narrow (e.g., about 0.060 inch wide) and relatively long (e.g., about 13 mm long), connects a relatively broad open loop (e.g., about 3 mm in diameter) to a collapsible anchor. Upon deployment, the protrusion pushes the open loop against the intestinal wall. Without being bound by any particular theory, initial research suggests that the muscle layer in the intestine stretches across the loop, and it eventually thins out or erodes enough to allow the loop to penetrate the luminal wall. A chronic inflammation response causes scar tissue to form around the loop and through the opening formed by the loop; this scar tissue can hold the loop securely. Because the loop is rounded or otherwise shaped to promote erosion through the muscle wall, the protrusion and the loop are less likely to pierce the scar tissue or surrounding organs.

Straight Protrusions with Open Loops

Figure 1B:
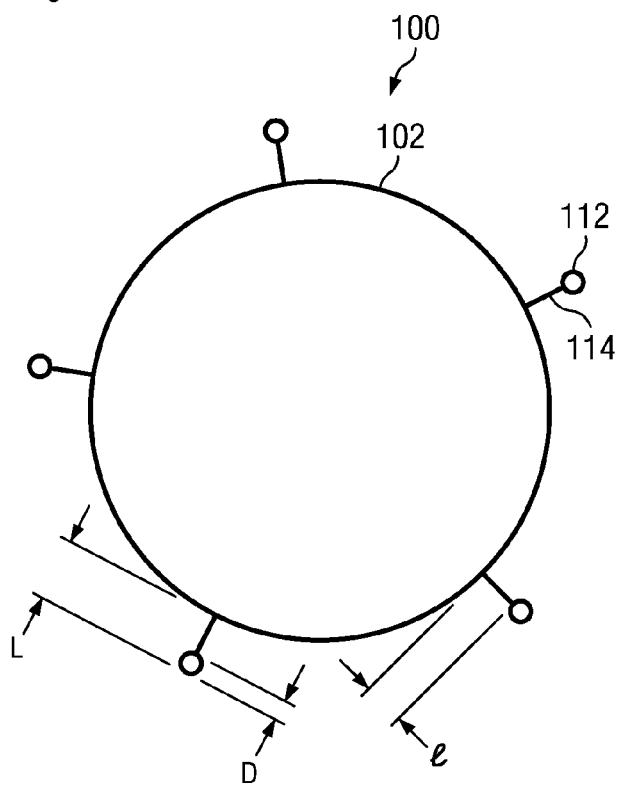
Figure 1C:
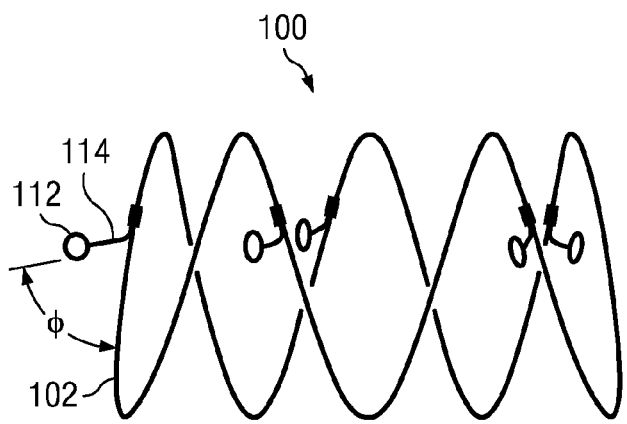
Figure 1D:
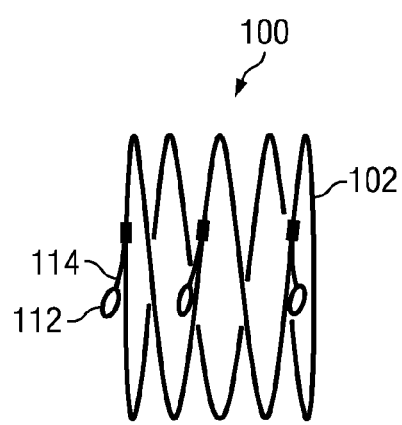
Figure 2A:
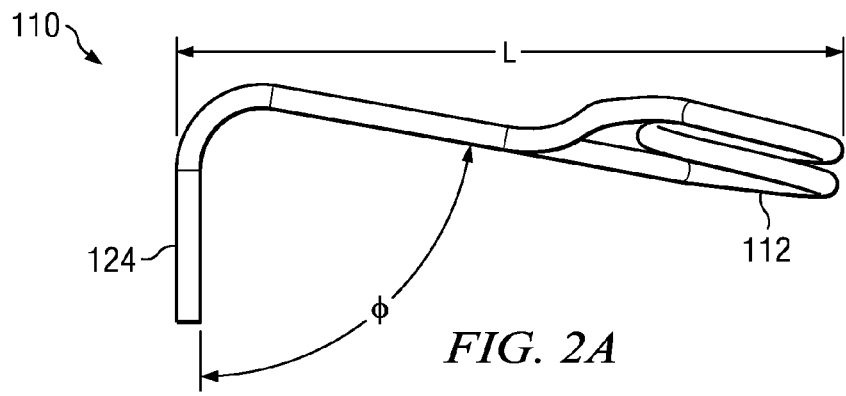
FIGS. 2A-2D are plan and elevation views of a straight protrusion with an open loop suitable for connection to an anchor.
Figure 2B:
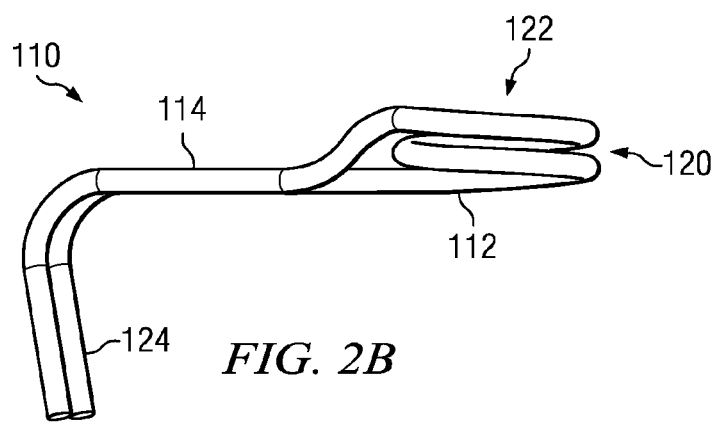
Figure 2C:
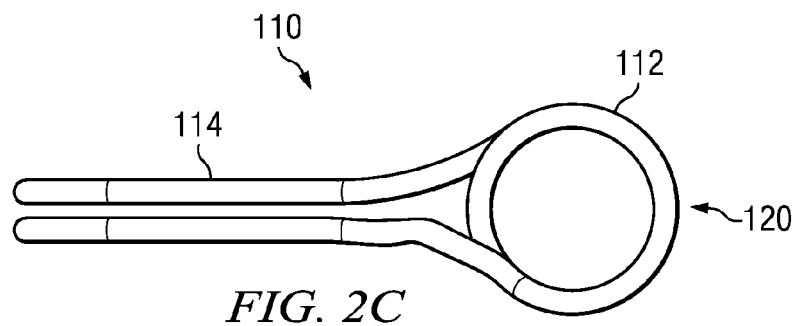
Figure 2D:
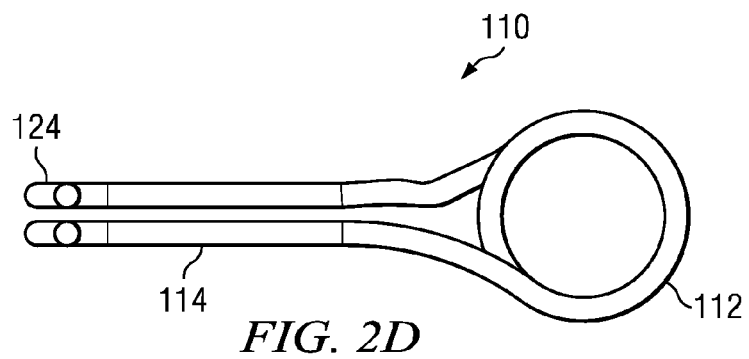

FIGS. 1A-1D show an implant 100 suitable for deployment within the gastrointestinal tract distal to the pylorus. FIGS. 1A-1C show perspective, plan, and elevation views of the implant 100 in a relaxed state (from the top, the relaxed implant 100 looks circular); FIG. 1D is an elevation view of the implant 100 in a compressed state. Typically, the implant 100 is compressed for endoscopic deployment within the gastrointestinal tract. Once positioned properly within the gastrointestinal tract, the implant 100 expands to the relaxed state shown in FIGS. 1A-1C.

The implant 100 includes a collapsible wave anchor 102 that includes a plurality of protrusions 110, each of which extends outward from the wave anchor 102 when the implant 100 is in a relaxed state. The anchor 102 may have a relaxed diameter of about 40 mm or greater, e.g., about 45 mm, about 50 mm, or about 55 mm. Each protrusion 110 includes a rounded loop 112 at the end of a narrow, straight neck 114, and each loop 112 includes an opening whose inner width D is within the range (inclusive) of between about 1 mm and about 13 mm, and preferably a diameter D within a range of about 1 mm and about 6 mm, or, more preferably, about 3 mm. The outer diameter can be within a range of about 2 mm to about 8 mm, and the diameter of the wire used to form each protrusion 110 can be within a range of about 0.010 inch to about 0.030 inch. Typically, the minimum bend radius of the wire limits the minimum inner diameter (it can be difficult to bend the wire too tightly), and the minimum desired pressure exerted by the loop 112 against the tissue limits the maximum inner diameter (bigger loops 112 may not exert enough pressure on the tissue to penetrate the tissue). The straight neck 114 has a length l of between about 6 mm and about 10 mm, for a total projection length L of between about 7 mm and about 13 mm. A crimp 116 or other suitable connection fixes the neck 114 to the wave anchor.

Each protrusion 110 folds down along the side of the wave anchor 102 when compressed for delivery, then springs up to extend nearly perpendicularly from the wave anchor 102 when released from the compressed state to the relaxed state. Specifically, the angle $\phi$ formed by the protrusion 110 and a leg of the wave anchor 102 may be between about 45° and about 135°, or, more preferably, between about 75° and 105°, e.g., about 80° or about 90°.

FIGS. 2A-2D are elevation and plan views of a single protrusion 110 formed of a single piece of nitinol wire with a diameter of about 0.020 inch. The wire is bent to form a pair of struts 124 that can be crimped, bonded, or welded onto a single-wire leg of an anchor (e.g., wave anchor 102 in FIGS. 1A-1D) such that the single wire of the anchor leg nestles between the struts 124. The wire is bent to form the narrow, straight neck 114 and coiled twice to create the loop 120. The two loops of coil form a broad, blunt edge 120 that can engage and erode the luminal wall such that the loop 112 eventually penetrates the luminal wall. In this case, the loops also form a face 122 that defines a plane perpendicular to the long axis of the struts 124. When affixed to an anchor and implanted in a lumen, the face 122 is perpendicular to the long axis of the lumen and parallel to a cross section of the lumen. Alternatively, the loop 112 may be formed such that the face 122 is parallel to the long axis of the struts 124. In this alternative orientation, the face 122 is near parallel to the lumen's long axis and near perpendicular to the lumen's cross section when implanted.

Figure 3A:
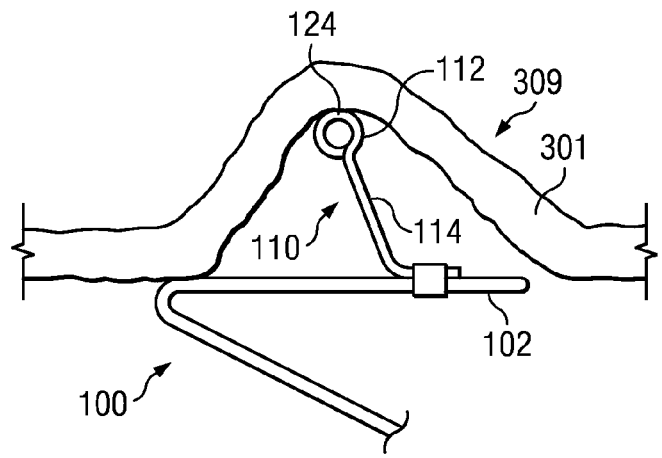
FIGS. 3A-3C illustrate how a straight protrusion with an open loop penetrates the wall of the gastrointestinal tract and how a fibrotic encapsulation forms about and through the open loop.
Figure 3B:
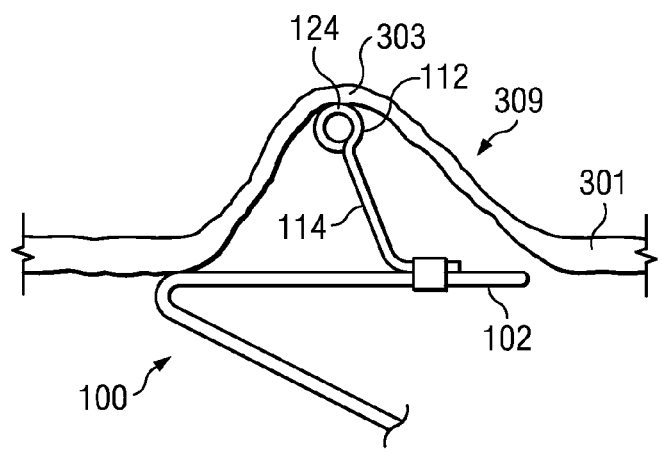
Figure 3C:
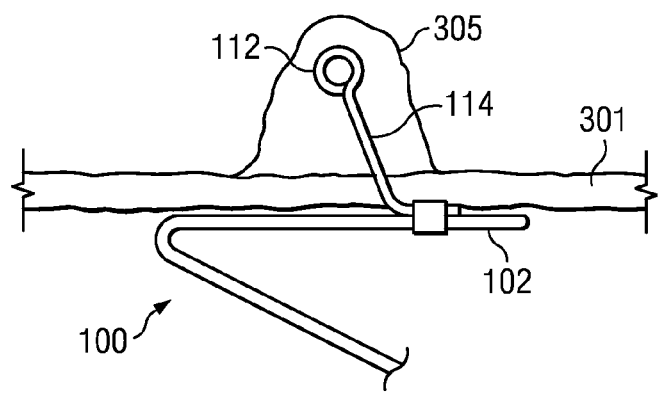

FIGS. 3A-3C illustrate how the implant 100 is secured within a lumen by a protrusion 110 with a relatively straight neck 114. First, the implant 100 is inserted into the lumen in a compressed state, with the projection 110 folded against the collapsed anchor 102. Once released into the lumen, the anchor 102 and the protrusion 110 expand toward their respective relaxed states, causing the edge 124 of the loop 112 to form a tent 309 in the luminal wall 301, which may include a muscle layer, as shown in FIG. 3A. Without being bound by a particular theory, initial studies suggest that, over time, the tent 309 stretches and the face 124 erodes at the point of contact 303, as shown in FIG. 3B. Eventually, the loop 112 erodes completely through the luminal wall 301, as shown in FIG. 3C. Within two to four weeks, fibrotic tissue 305 forms about and through the loop 112, securing the loop 112 with respect to the luminal wall 301, and may secure the loop 112 in a permanent or quasi-permanent fashion (e.g., for months or years). A loop 112 that is secured in a pocket of fibrotic tissue 112 does not appear to provoke the tissue remodeling that eventually forces other projections, such as sharp protrusions, out of the intestine.

Figure 4A:
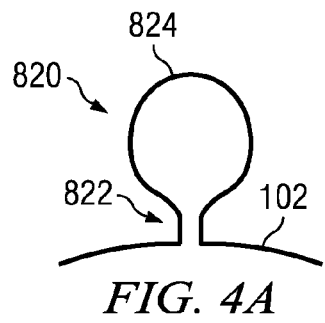
FIGS. 4A-4P show various alternative protrusions with open loops.
Figure 4B:
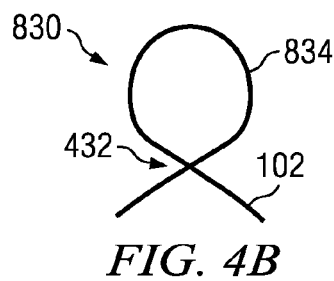
Figure 4C:
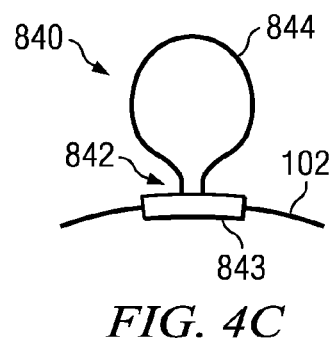

FIGS. 4A-4C show open-loop protrusions of different shapes. FIG. 4A shows a protrusion 820 formed by bending wire into the shape of the Greek letter omega, Ω. An open, straight neck 822 connects the protrusion's loop 824 to a collapsible member 102. FIG. 4B shows a protrusion 830 formed by twisting wire into a loop. The twist forms the protrusion's neck 432 and the loop forms the protrusion's loop 834. FIG. 4C shows a protrusion 840 with a neck 842 covered by a seal 843. The seal 843, which may be made of a fluoropolymer, isolates the loop 844 from the anchor 102, and may prevent irritants from exiting the luminal wall via the channel formed by the protrusion 840. The seal 843 does not cover the loop 844, so tissue may grow through the loop 844. The protrusions 820, 830, and 840 shown in FIGS. 4A-4C may be separate pieces of wire bonded to an anchor or they may be formed of the same piece of wire that forms the anchor.

Figure 4D:
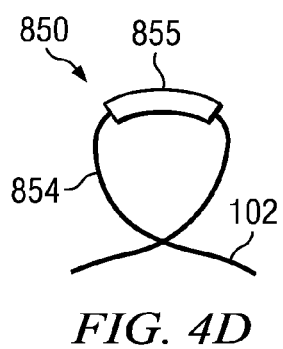
Figure 4E:
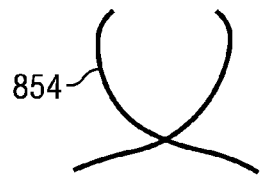

FIGS. 4D and 4E show an open-tip protrusion 850 with an erodible section 855 that forms part of a loop 854 connected to an anchor with a straight neck. After the protrusion 850 penetrates the luminal wall, inflammatory or fibrotic tissue grows through the loop 864, securing the protrusion 850 in the intestinal wall. Meanwhile, the erodible section 855 dissolves, turning the loop 854 into an open prong that can removed from tissue without tearing the tissue (not shown) that forms in the opening of the loop 854. Typically, the erodible section 855 is designed to dissolve during treatment, e.g., over six months, one year, two years, or possibly longer.

Figure 4F:
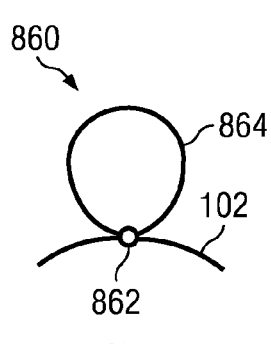
Figure 4G:
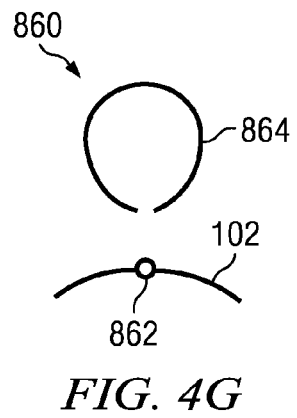

FIGS. 4F and 4G show an open-tip protrusion 860 with a loop 864 that can be detached from an anchor 102 with a narrow coupling neck 862. As above, inflammatory or fibrotic tissue (not shown) envelops the loop 864, securing the protrusion 860 in the intestinal wall. By disconnecting the anchor 102 from the protrusion 860, the anchor 102 can be withdrawn endoscopically without tearing or ripping the tissue that envelops the loop. In some cases, the detached anchor 102 may be reinserted into the intestine and re-attached to the protrusion 860.

Figure 4H:
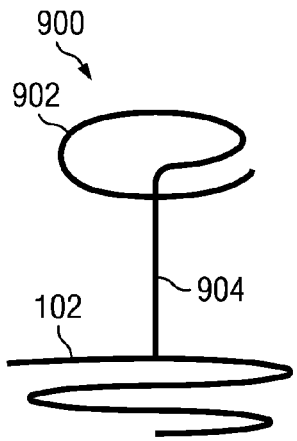
Figure 4I:
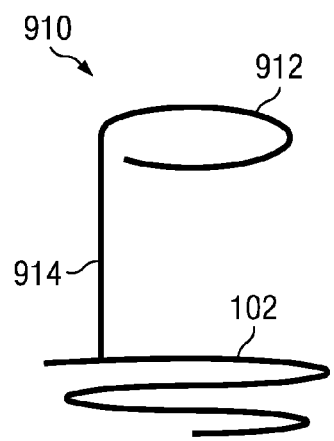
Figure 4J:
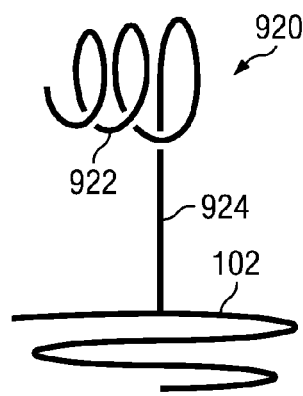
Figure 4K:
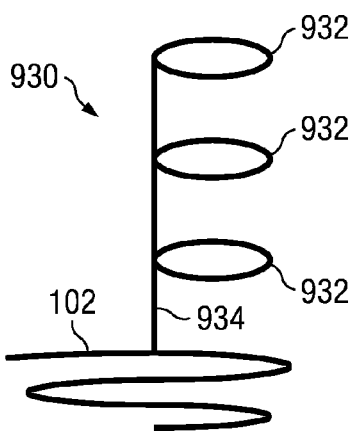

FIGS. 4H-4O show alternative straight protrusions with open heads. FIGS. 4H and 4I shows protrusions 900 and 910, respectively, with open loops 902 and 912 that define planes parallel to the lumen wall when deployed. The open loop 902 of FIG. 4H is made of a wire loop that is concentric about an axis of a straight neck 904; whereas, the open head 912 of FIG. 4I is formed of a wire loop that is tangent to an axis of a straight neck 914. FIG. 4K shows a straight protrusion 930 with plural open loops 932 distributed along the length of a straight protrusion 934 that extends from a collapsible anchor 102.

FIG. 4J shows a protrusion 920 with a corkscrew-like open head 922 perched atop a straight neck 924 coupled to an anchor 102. When deployed, the long axis of the open head 922 is roughly parallel to the long axis of the lumen, but can also be oriented perpendicular to the long axis of the lumen. Similarly, FIG. 4N shows a protrusion 960 with a whisk-shaped open head 962 at the end of a straight neck 964. Tissue may grow about and through the openings between the windings in both the corkscrew-like head 922 and the whisk-shaped head 962, just as in the helix protrusions described in greater detail below.

Figure 4L:
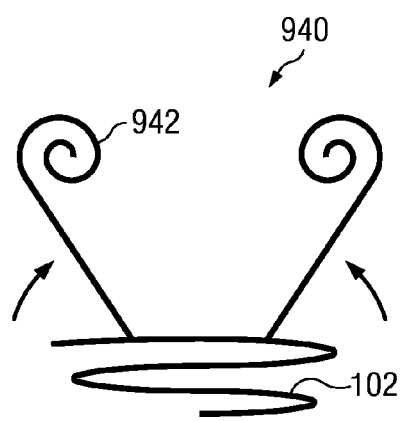
Figure 4M:
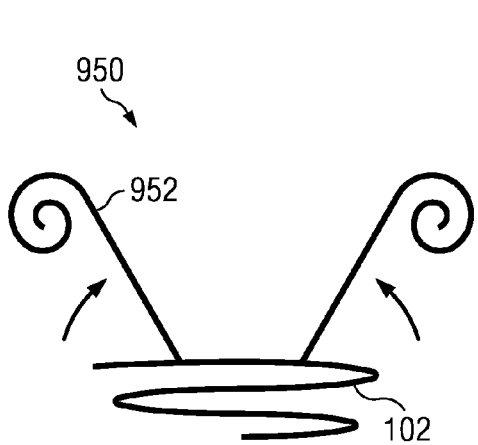
Figure 4N:
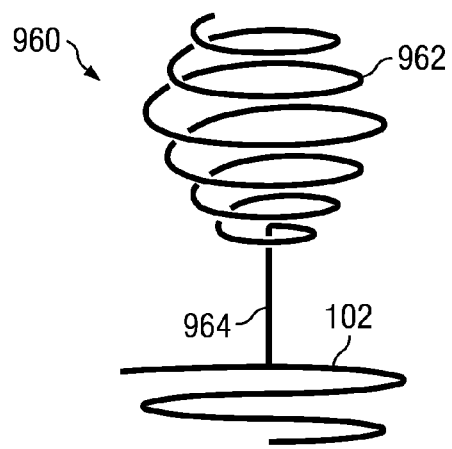

FIGS. 4L and 4M show bidirectional protrusions 940 and 950, respectively, each of which is coupled to a collapsible anchor 102. Each protrusion 940, 950 includes a coil-like open head 942, 952 that engages the luminal wall as the protrusion 940, 950 expands from its collapsed state.

Figure 4O:
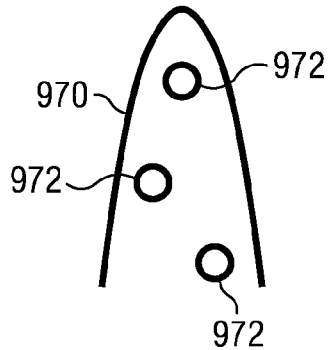

FIG. 4O shows an alternative protrusion 970 formed of a paddle with one or more openings 972, each of which is about 0.016 inch wide. Tissue can form through the openings 972 to secure the protrusion 970 within the lumen.

Figure 4P:
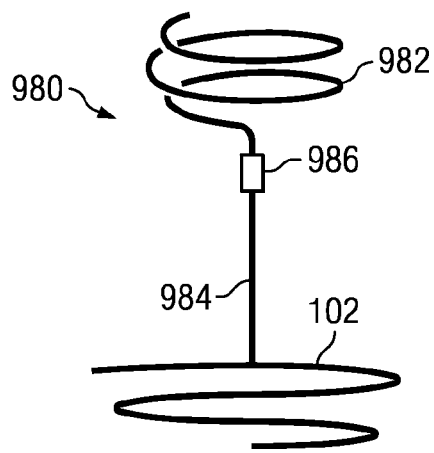

The open heads may also be connected to the anchor with a detachable or erodible feature. FIG. 4P shows a protrusion 980 that includes a coiled open loop 982 connected to a straight neck 984 with a bio-erodible element 986. Upon deployment, the loop 982 erodes through the luminal wall and soon becomes encased in fibrotic tissue, securing the protrusion 980 and attached anchor 102 in place. Over time, the bio-erodible element 986 dissolves, causing the loop 982 to become detached from the protrusion 980. Once the head 982 is no longer connected to the protrusion 980, the protrusion 980 can be withdrawn without necessarily tearing the scar tissue encapsulating the head 982, making for easier removal of the implant.

Helical Protrusions with Open Loops

Alternatively, the implant may include a helical protrusion instead of a straight protrusion. The helical protrusion acts as a coil spring that pushes the open loop into the lumen wall, but in a manner that distributes the load from the collapsible anchor to the contacting tissue over a longer length as compared to a straight protrusion of similar height. Upon initial engagement with the duodenal wall, the helix, if so designed, compresses. As the tissue and helix protrusion come to equilibrium the helix approaches full expansion, causing the loop to penetrate the luminal wall. Eventually, fibrotic tissue encapsulates the loop and the expanded helix, creating a pocket that holds the loop and helix securely. Like straight protrusions with open loops, helical protrusions with open heads may be designed for permanent, quasi-permanent, or temporary implantation.

Figure 5A:
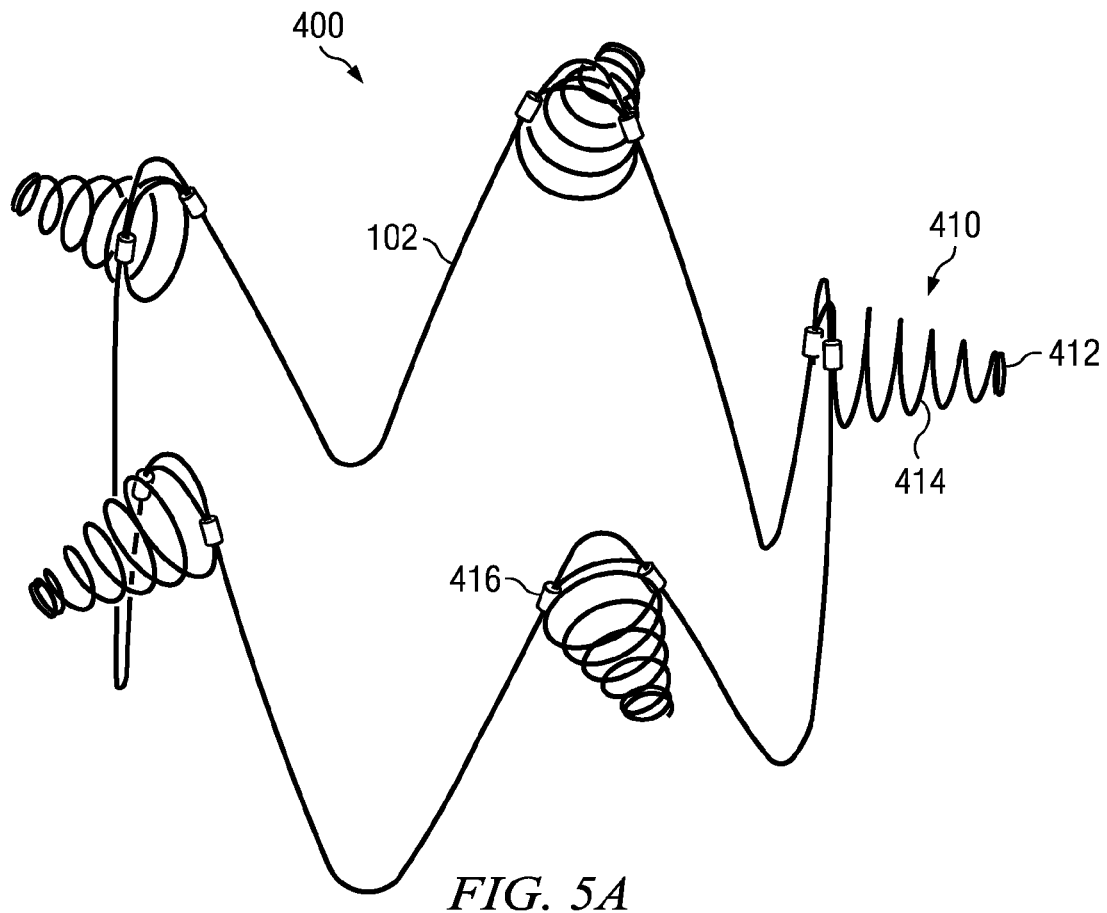
FIGS. 5A-5C are perspective views of wave anchors with helical protrusions with open loops.
Figure 5B:
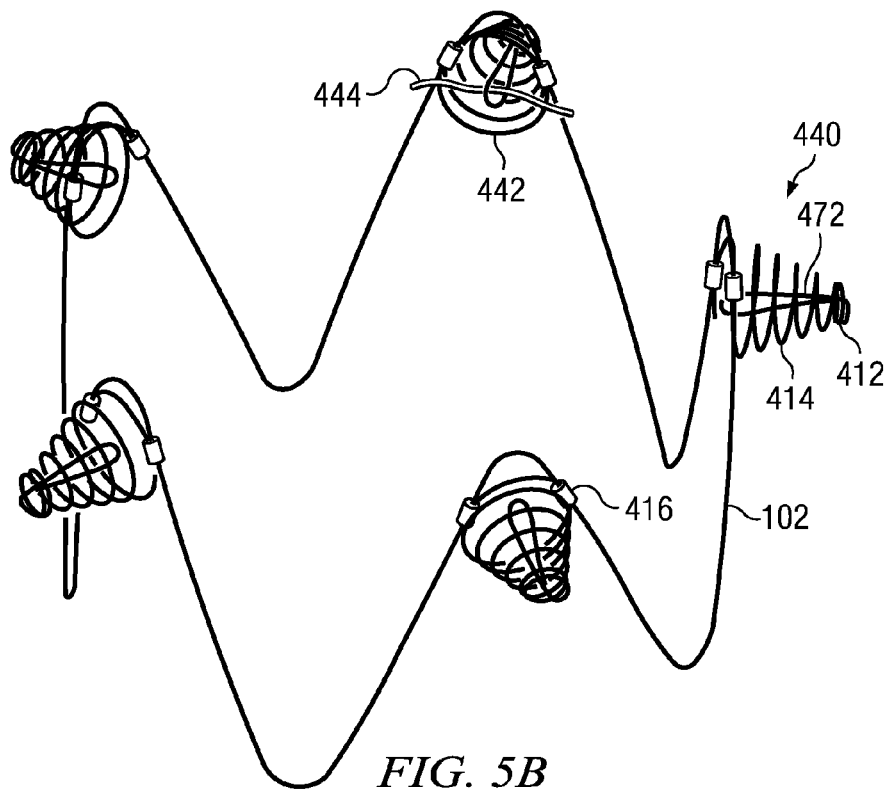
Figure 5C:
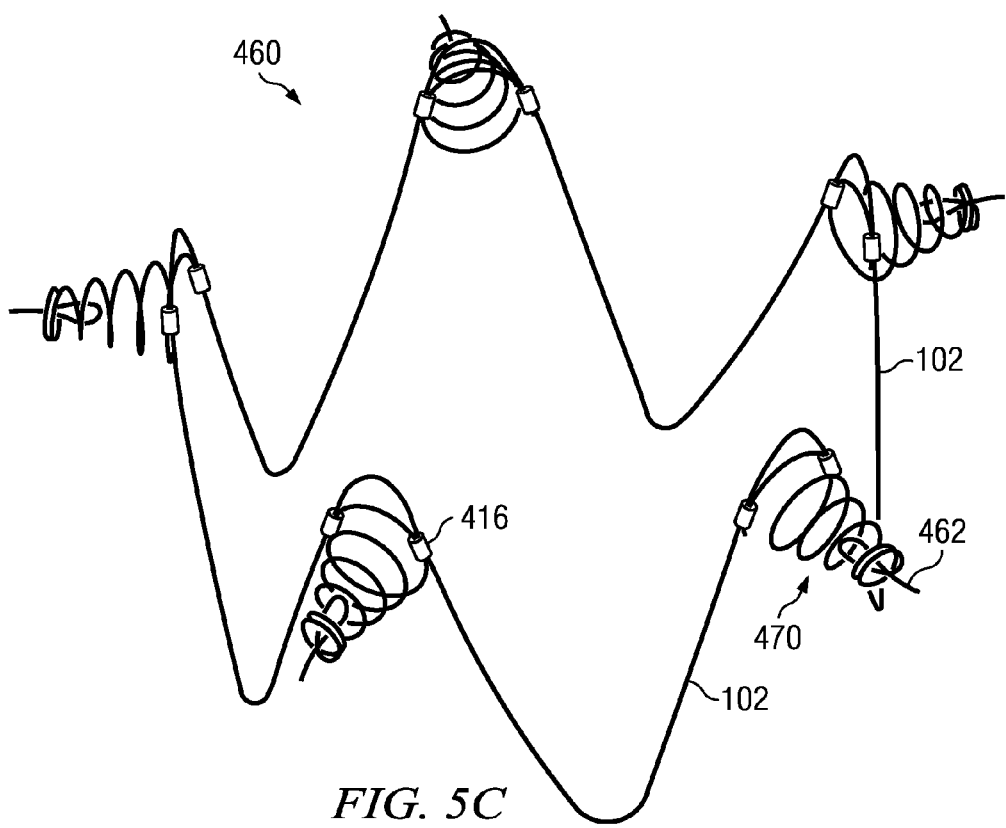

FIGS. 5A-5C are perspective views of implants that include projections with helical protrusion: FIG. 5A shows basic helical protrusions; FIG. 5B shows helical protrusions with retaining loops; and FIG. 5C shows helical protrusions that include retaining loops and short end effects that promote initial penetration of the open loop into the muscle wall. FIG. 5A shows an implant 400 that includes five basic helical protrusions 410, each of which is coupled to a wave anchor 102 with a respective crimp 416. (Alternatively, the protrusions 410 may sutured or releasably coupled to the anchor 102.) Each helical protrusion 410 includes a helix 414 formed of several wire coils and terminates in a loop 412 formed of two loops of wire. The opening of each head 412 is parallel to the lumen defined by the wave anchor 102. Each helical protrusion 410 has a tapered profile, with the top coils (i.e., those farthest away from the wave anchor 102) being substantially smaller than the base coils (i.e., those closest to the wave anchor 102). Each coil in the helix 414 limits the penetration of the coil above it.

The top coils are sized to focus the force from the expanding implant 400 to penetrate the duodenal wall and to ultimately elicit the healing response. Top coils approximately 3 mm in diameter are small enough to start to burrow through the muscle layer. The base coils are larger than the top coils and are sized to substantially match and blend to the crowns (vertices) of the wave anchor 102. For example, a 7 mm diameter base coil blends well to the wave anchor 102 approximately 6 mm below the crowns, but larger base coils could be used for other attachment configurations and/or anchor configurations. Typically, the outer diameter of the largest coil in the helix 414 is within the range of about 1.5 mm to about 12 mm, and the coils have an inner diameter that ranges from about 1.0 mm to about 10 mm. The loop 412 can have an inner diameter within a range of about 1.0 mm and about 6.0 mm.

The spacing of the coils or wire wraps in the helix 414 influences the tissue response. If the coils are too close together, then tissue may not be able to grow around the wire or between the coils. If the coils are too far apart, then each coil may exert more localized force on the tissue, causing the tissue to erode at the point of contact. In addition, increasing the coil spacing makes it more likely that the upper coils will infiltrate surrounding organs. Setting the spacing between wraps, or coil pitch, within a range of about 1.0 mm to about 4.0 mm (or, more preferably, within a range of about 2.4 mm to about 2.5 mm), limits the erosion caused by the upper coils while allowing for tissue encapsulation of helix 414.

In the examples shown in FIGS. 5A-5C, the loop 412 is formed of two coils of uniform diameter that are stacked upon each other, approximating a solid cylinder that does not compress. Because the loop 412 is relatively incompressible, it erodes through the duodenal wall, but only to an extent determined by the length and compliance of the helix 414. A helix 414 with appropriate compliance typically prevents the loop 412 from penetrating much beyond the muscle layer of the duodenal wall.

FIG. 5B shows an implant 430 with several projections 440, each of which includes a retrieval element 442 that extends from the loop 412 towards the wave anchor 102. In the example shown in FIG. 5B, the retrieval element 442 is a loop of wire formed with an optional hypodermic tube 472, which provides an additional surface for fibrotic tissue to encapsulate; this further encapsulation may increase the anchoring strength. Each retrieval element 442 fits in the conical cavity defined by its associated helical neck 414 and can be used to exert a force normal to the axis of the conical cavity on the helical protrusion 410. For example, a normal force can be used to prevent or slow expansion of the helical protrusion 410 or to collapse an expanded helical protrusion 440. Other retrieval elements may be hooks, balls, or other suitable features for applying a normal force to the helix.

In the example shown in FIG. 5B, a constraint 444 threaded through the retrieval element 442 keeps the helical protrusion 440 in a fully or partially collapsed state. In some cases, the constraint 444 is a suture or biodegradeable element that allows the user to influence how quickly the helical protrusion 440 expands after implantation, which, in turn, affects how quickly the loop 412 penetrates the luminal wall. Releasing tension on the suture or engineering the decay time of the biodegradable element allows the helix 414 to open to its full height more slowly, prolonging the equilibrium time and slowing the effect of the helical protrusion 440 on the contacting tissue.

A drawstring (not shown) that runs through some or all of retrieval elements 442 can be used to withdraw the protrusions 440 from the luminal wall. Pulling on the drawstring applies a normal force directly to the loops 412, causing the loops 412 to collapse into the coils below to disengage the helix 414 from the surrounding tissue. As the coils collapse, one within the next, they act as a "cheese cutter": each coil helps to shear the surrounding tissue from the coil above it as the above coil passes through the lower coil, freeing the helical protrusion 440 from any scar tissue that may have grown through or around the wire in the loop 412 and the helix 414. Pulling on the drawstring also causes the anchor 102 to collapse for endoscopic withdrawal from the implantation site as described below.

FIG. 5C shows an implant 460 with an end effect 462 at the end of each helical protrusion 470. In this example, each end effect 462 is a post that is oriented in the center of a respective helical protrusion 470 and protrudes slightly beyond the loop 412 of the respective helical protrusion 470. The end effects 462, which may be sharpened to engage the contacting tissue more quickly, initiate an injury to the duodenal wall and lead the heads 412 through the duodenal wall. Because each end effect 462 pierces the luminal wall, it initiates the injury that causes fibrotic tissue to encapsulate its associated helical protrusion 470 more quickly. Quickly embedding the helical protrusion 470 is important for stabilizing and maintaining placement of the implant in a mobile vessel with pressurized luminal contents, such as the duodenum or intestines.

Figure 6:
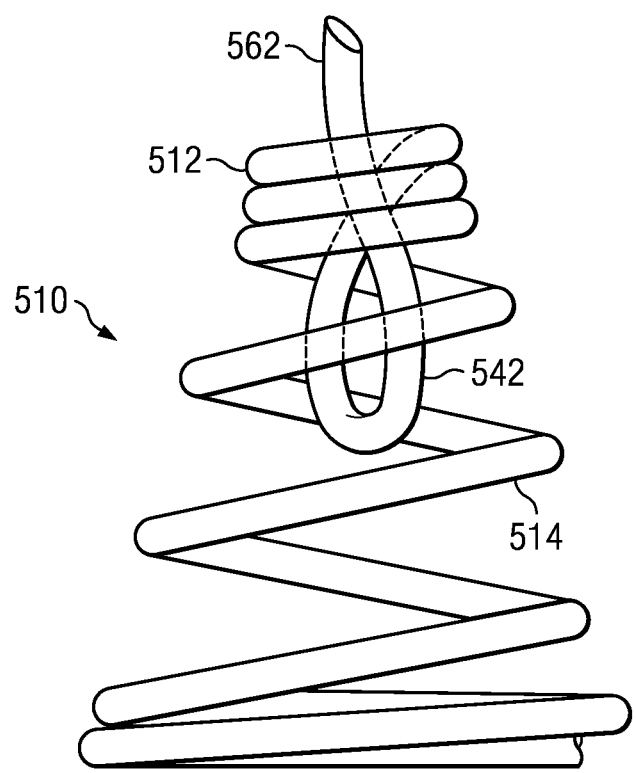
FIG. 6 is a perspective view of a loop projection with a helical neck.

FIG. 6 is a perspective view of an alternative helical protrusion 510 with a retrieval element 542 formed of a single wire without a hypodermic tube. The wire is coiled to form a helix 514 and a loop 512, then folded and formed into a retrieval element 542. Excess wire extending from the tail of the retrieval element 542 is trimmed and may be sharpened to create an end effect 562. The base coil of the helix 414 can be trimmed and/or bent as necessary before the projection is attached to the wave anchor 102, e.g., with a crimp 416, as shown in FIGS. 5A-5C, or using any other suitable attachment. Alternatively, the helical protrusion can be fabricated with a post that runs up its center, and the post can be crimped or otherwise affixed to the anchor 102.

Figure 7A:
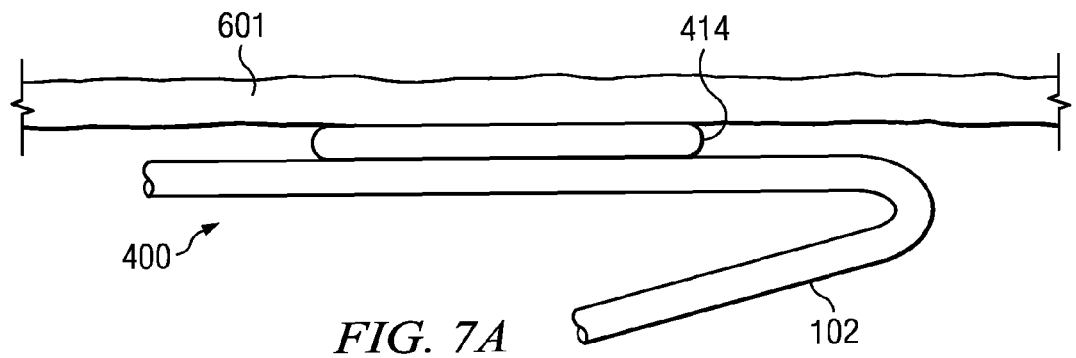
FIGS. 7A-7C illustrate how a helical protrusion with an open loop penetrates the wall of the gastrointestinal tract and how a fibrotic encapsulation forms about and through the helical protrusion and the open loop.
Figure 7B:
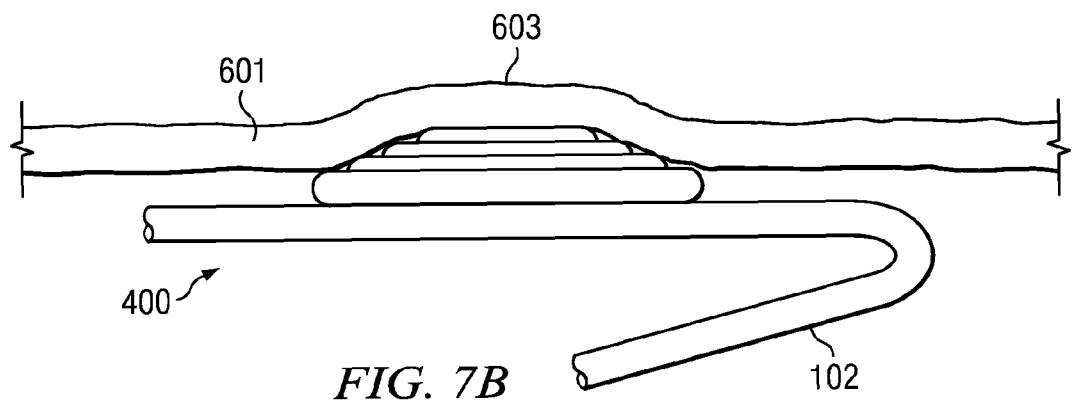
Figure 7C:
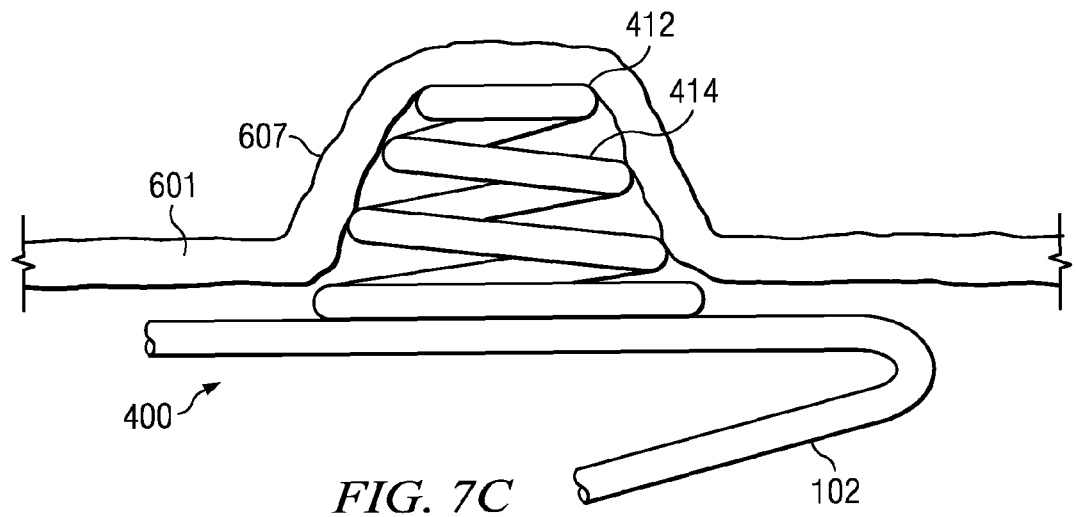

FIGS. 7A-7C show how the helical protrusion 410 shown in FIG. 5A engages a luminal wall to secure an implant 400 within the lumen. The implant 400 is inserted into the lumen in a compressed state, with the helical protrusion 410 collapsed against the collapsed anchor 102, as shown in FIG. 7A. Releasing the helical neck 414 allows the helical neck 414 to expand, causing a tent 603 to form in the duodenal wall 601, as shown in FIG. 7B. As the neck 414 continues to expand against the duodenal wall 601, it pushes the loop 412 through wall 601, as shown in FIG. 7C. Scar tissue 607 forms about and possibly through the loop 412 and neck 414. Without being bound by any particular theory, initial studies suggest that helical necks 414 tend to encourage more fibrotic encapsulation than straight necks of similar height because helical necks have more wire in contact with the tissue.

The compliance of the helical neck 414 affects how quickly the loop 412 penetrates the luminal wall 601. Initial studies suggest that the top-most coils in the helical neck 414 continue to push through tissue after initial contact until the contacting tissue and helix 414 come to equilibrium. If the helical neck 414 is as compliant as the luminal wall, however, then the neck 414 will not be able to push the loop 412 through the luminal wall 601. Since the compliance of the helical neck 414 is largely a function of wire diameter and pitch, increasing either the wire diameter or the pitch the wire diameter generally increases the rigidity of helical neck 414. Increasing the wire diameter too much may make it difficult to form the wire into tight loops to shape the loop 412. Wire with a diameter in the range of about 0.016 inch to about 0.040 inch is generally suitable for helical protrusions 410. Nitinol wire with a diameter of about 0.019" offers a balance: it can be formed into tight bends for the end of the helical neck 414 and the loop 412, yet forms a helix that is stiffer than the luminal wall 601. It can also be packed into a capsule for endoscopic delivery. The diameter of the helix 414 can also be varied to further customize the transition in stiffness and tissue response.

Although FIGS. 5-7 show a helix 414 with a linear transition between successive coil diameters, alternative helixes can have other shapes, including parabolic profiles, cylindrical profiles, hourglass profiles, and conical profiles (e.g., with the vertex of the cone connected to the anchor). Alternatively, the helix 414 can be formed in a flattened coil that is narrow at the center and flares out from the center into a flat spiral shape. The helix 414 could also be formed of a post that terminates in a coil with its wrappings aligned or angled with respect to one another in a corkscrew-like fashion. Compared to other three-dimensional shapes, tapered shapes tend to be easier to disengage from a mating surface. Parabolic shapes transition more quickly from large coils to small coils, facilitating a lower profile protrusion. Similarly, transitions between coils or wraps in the helix 414 can be customized as desired. For example, the coils in the helix 414 can be sized such that each coil fits into the coil below. This sizing of successive coils facilitates a lower profile for packing into the delivery catheter and facilitates disengagement from the duodenal wall.

Compliance Measurements

The compliance/stiffness of the protrusions disclosed herein can be characterized, in part, by the force required to deflect the protrusions from their respective relaxed (extended) states towards their respective collapsed states. For a protrusion with a straight neck (e.g., protrusion 110 of FIGS. 2A-2D), compliance may be defined, in part, by the normal force required to deflect the protrusion at room temperature by a given amount towards the strut of the collapsible anchor. Measurement shows that applying a force of at least about 0.1 lbf normal to the head (i.e., parallel to the long axis of the lumen) completely collapses a straight-necked protrusion made of 0.010-inch diameter nitinol wire, with a total length of 13 mm, ending in a loop formed of two wraps of wire with an inner diameter of about 3 mm. Similar measurement shows that applying about 0.8 lbf normal to the head deflects the head by about 0.250 inch for a straight-necked protrusion made of 0.020-inch diameter nitinol wire, with a total length of 11.5 mm, ending in a loop formed of two wraps of wire with an inner diameter of about 3 mm. Other straight-necked protrusions may be deflected by about 0.250 inch from their relaxed positions by forces within a range of about 0.80 lbf to about 0.95 lbf.

The compliance of a helical protrusion can be characterized, in part, by measuring the force required to (partially) collapse the helical protrusion at room temperature. Measurement shows that applying a force normal to the long axis of a helical protrusion within a range of about 0.19 lbf to about 1.75 lbf, or, more preferably, about 0.32 lbf to about 0.95 lbf, collapses the protrusion by about 0.250 inch, depending on the wire diameter, coil pitch, and coil size:

TABLE 1

Normal force applied to compress nitinol helical protrusions by 0.250 inch at room temperature

| Protrusion Height | Base Coil Diameter | Top Coil Diameter | Coil Spacing | Wire Diameter | Normal Force |
|---|---|---|---|---|---|
| 10 mm | 6 mm | 3 mm | 2.4 mm | 0.016" | 0.19 lbf |
| 6 mm | 6 mm | 3 mm | 4.0 mm | 0.023" | 0.32 lbf |
| 10 mm | 6 mm | 3 mm | 2.4 mm | 0.028" | 0.95 lbf |
| 10 mm | 6 mm | 3 mm | 2.4 mm | 0.030" | 1.75 lbf |

In addition to the compliance of the helix as measured in the normal force to compress the helix, resistance to bending must be considered. Helix stiffness can also be characterized by the force required to deflect the helix sideways, i.e., in the plane normal to the long axis of the helix. A balance must be struck between compressability and rigidity. Deflecting a nitinol helical protrusion with a 6 mm height, 6 mm base coil diameter, 3 mm top coil diameter, 4.0 mm coil spacing, and 0.020-inch wire diameter sideways by 0.250 inch at room temperature takes a force of at least about 0.033 lbf. Increasing the wire diameter to about 0.028 inch increases the force to about 0.135 lbf for a 0.250-inch deflection at room temperature. A preferred balance can be defined within the specifications above.

Deployment and Removal of Anchors Secured with Loops and Necks

Each of the aforementioned implants may be deployed in the intestine, preferably in the duodenum, and more preferably in the duodenal bulb just distal to the pylorus. Typically, a doctor or other qualified person inserts the implant into the intestine with an endoscopic delivery device. During insertion, the delivery device holds the implant in a compressed state. Once in position, the implant is released from the delivery device and allowed to self-expand, causing each neck coupled to the anchor to push its respective loop against the intestinal wall. Some implants may include a sleeve coupled to the anchor, which can be deployed within the intestine as described in U.S. Pat. Nos. 7,122,058; 7,329,285; 7,678,068; and U.S. patent application Ser. No. 11/057,861, filed on Feb. 14, 2005, by Levine et al., all of which are incorporated herein by reference in their entireties.

An implant secured with protrusions tipped with open loops may be removed laparoscopically, surgically, or, more preferably, endoscopically with an endoscope.

For example, an implant may be collapsed using a drawstring, then withdrawn from the intestine using an endoscope. Further details on endoscopic removal can be found in U.S. application Ser. No. 11/318,083, filed on Dec. 22, 2005, by Lamport and Melanson; and in U.S. application Ser. No. 12/005,049, filed on Dec. 20, 2007, by Levine et al., both of which are incorporated herein by reference in their entireties.

Seals, Sleeves, and Restrictor Plates

Figure 8:
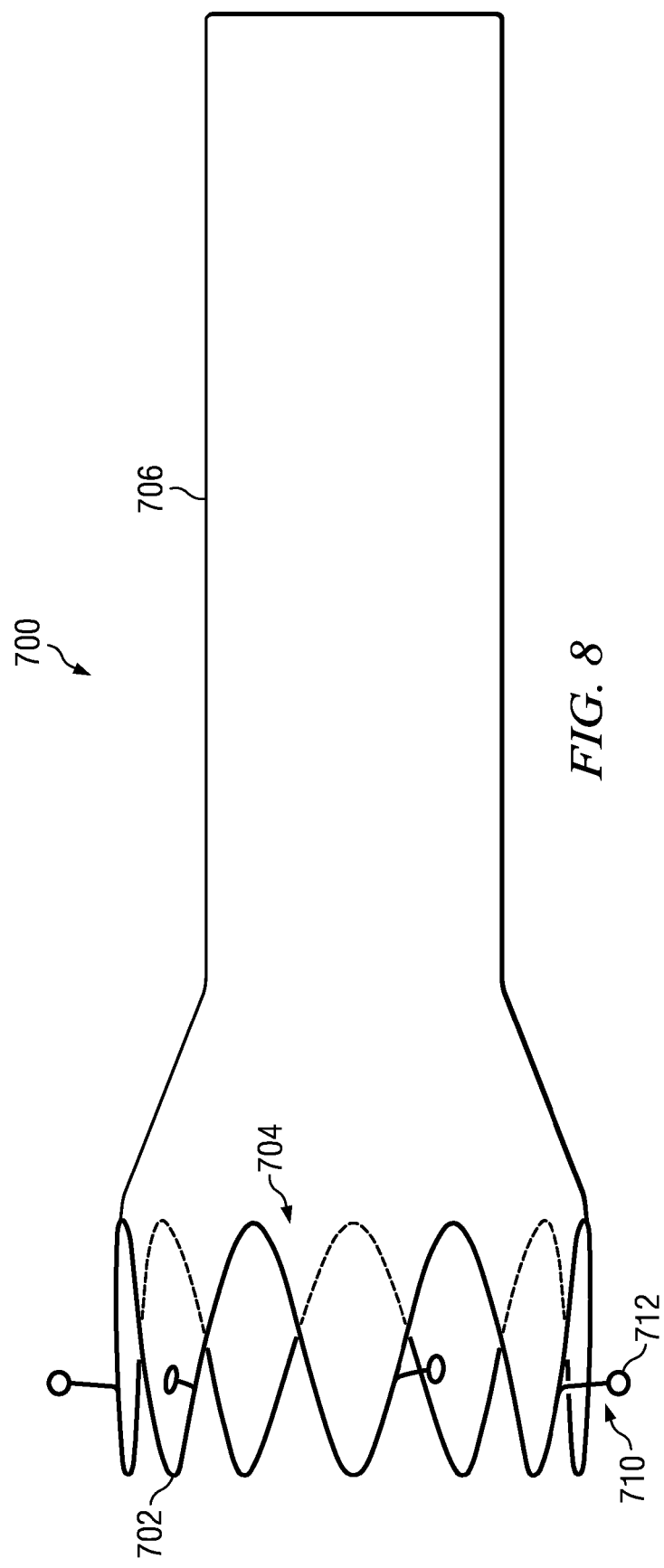
FIG. 8 shows an implant that includes a sleeve extending from an anchor with open-tip protrusions.

FIG. 8 shows an implant 700 that includes an anchor 702 with a polymer covering 704. Protrusions 710 projecting from the anchor 702 support open loops 712 that can be used to create fibrotic encapsulations in the intestinal wall as described above. A sleeve 706 is coupled to the distal side of the anchor 702 for extension into the intestine. The sleeve 706 may be permanently or detachably affixed to the anchor 702. For instance, a detachable sleeve can be endoscopically attached to or removed from a permanently or semi-permanently secured anchor depending on treatment progress.

Typically, the sleeve 706 is floppy and conformable to the wall of the intestine when deployed. It also has a wall thickness of less than about 0.001 inch to about 0.005 inch and a coefficient of friction of about 0.2 or less. The polymer covering 704 and the sleeve 706 may be made of a fluoropolymer, such as ePTFE coated or impregnated with fluorinated ethylene polyethylene (FEP), or any other suitable material. The sleeve 706 and anchor covering 704 can be a single, integrally formed piece. They can also be separate pieces, depending on whether the anchor 702 is partially or wholly uncovered, as long as the anchor 702 forms a sufficiently good seal between the sleeve 706 and the stomach, pylorus, and/or intestine to funnel chyme through the sleeve 706. Each loop 712 remains uncovered or only partially covered to promote the in-growth of fibrotic tissue.

Anchors secured with loops and necks may also be used to secure restrictor plates within the gastrointestinal tract to treat obesity, such as the restrictor plates disclosed in U.S. patent application Ser. No. 10/811,293, filed on Mar. 26, 2004, by Levine et al.; U.S. patent application Ser. No. 11/330,705, filed on Jan. 11, 2006, by Levine et al.; and U.S. patent application Ser. No. 11/827,674, filed on Jul. 12, 2007, by Levine et al., all of which are incorporated herein by reference in their entireties. An implant with a restrictor plate typically includes a restricting aperture that retards the outflow of food from the stomach to the intestine. The diameter of the aperture is less than 10 mm, is preferably less than 7 mm, and is more preferably initially in the range of about 3-5 mm. Alternatively, the aperture may be elastic and expandable under pressure from material flowing through the anchor and the aperture at elevated physiological pressures; as pressure increases, the aperture opens to greater diameters. The implant may include a sleeve that extends into the intestine.

While this invention has been particularly shown and described with references to example embodiments thereof, it will be understood by those skilled in the art that various changes in form and details may be made therein without departing from the scope of the invention encompassed by the appended claims. For example, all or part of the protrusions described above can be covered to further control interaction with contacting tissue. A bio-absorbable suture or adhesive could be used to affix the covering to the protrusion. As the bio-absorbable material degrades or is absorbed by the body, the covering is free to fan open, creating an added level of control of interaction between the protrusion and the surrounding tissue. Alternatively, the protrusion may be made from a polymer or a composite material, such as a non-degradable or biodegradable material. Implants can also include different types of protrusions, e.g., any combination of straight protrusions with open loops, helical protrusions with open loops, and even pointed barbs.

What is claimed is:

1. An implant comprising:
   a collapsible anchor configured to be deployed within a lumen of a gastrointestinal tract, the collapsible anchor having a relaxed diameter of at least 40 mm; and
   a protrusion having a first end connected to the collapsible anchor and a second end formed in a loop defining an opening for tissue ingrowth, the protrusion having a length of at least 5 mm, the protrusion including an extension that connects the loop to the collapsible anchor, the protrusion expanding from a collapsed state, in which the extension having the loop is collapsed alongside the anchor, to a relaxed state, in which the protrusion extends outward from the anchor upon deployment within the gastrointestinal tract, the loop having a blunt edge to engage a wall of the lumen, and the protrusion configured to, upon deployment, cause the blunt edge of the loop to form a tent in the wall of the lumen, the tent, over time, stretching the wall of the lumen and the blunt edge eroding the wall of the lumen at a point of contact, fibrotic tissue forming about the loop to secure the loop with respect to the wall of the lumen.

2. The implant of claim 1 wherein the protrusion includes a straight neck that connects the loop to the collapsible anchor.

3. The implant of claim 1 wherein the protrusion includes a helix that connects the loop to the collapsible anchor.

4. The implant of claim 3 wherein the helix has a tapered profile.

5. The implant of claim 3 further including a constraining element configured to maintain the helix in a collapsed state.

6. The implant of claim 3 further including:
   an end effect at a tip of the loop.

7. The implant of claim 1 wherein the loop defines an opening with an inner width within a range of 1 mm to 13 mm.

8. The implant of claim 1 wherein the loop defines an opening with an inner diameter of 3 mm.

9. The implant of claim 1 wherein the protrusion extends between 6 mm and 13 mm from the collapsible anchor upon full deployment from the collapsible anchor.

10. The implant of claim 1 wherein the loop is formed of wire with a diameter of 0.010 inch to 0.040 inch.

11. The implant of claim 1 wherein, in a relaxed state, the protrusion extends outwards from the collapsible anchor at an angle of between 45 degrees and 135 degrees.

12. The implant of claim 11 wherein, in a relaxed state, the protrusion extends outwards from the collapsible anchor at an angle of 80 degrees.

13. The implant of claim 1 wherein the loop defines a plane that is perpendicular to the wall of the lumen.

14. The implant of claim 1 wherein the loop defines a plane that is parallel to the wall of the lumen.

15. The implant of claim 1 wherein the loop is formed of a wire loop at an end of the protrusion.

16. The implant of claim 1 further including:
   a drawstring configured to collapse the protrusion towards the collapsible anchor to disengage the protrusion from the tissue.

17. The implant of claim 1 further including additional protrusions connected to the collapsible anchor, each additional protrusion having an end formed in a loop.

18. The implant of claim 1 wherein the collapsible anchor is a wave anchor.

19. The implant claim 1 further including:
   an unsupported, thin-walled sleeve coupled to the collapsible anchor and configured to extend into the lumen upon deployment of the collapsible anchor.

20. The implant of claim 1, wherein fibrotic tissue forms about and through the loop in a range of 2-4 weeks.

21. A method of securing a collapsible anchor within a lumen of a gastrointestinal tract, the method comprising:
   deploying the collapsible anchor within the lumen, the collapsible anchor including a protrusion having a first end coupled to the collapsible anchor and a second end formed in a loop defining an opening for tissue ingrowth, the protrusion including an extension that connects the loop to the collapsible anchor, the protrusion expanding from a collapsed state, in which the extension having the loop is collapsed alongside the anchor, to a relaxed state, in which the protrusion extends outward from the anchor upon deployment within the gastrointestinal tract, the loop having a blunt edge to engage a wall of the lumen; and causing the blunt edge of the loop to form a tent in the wall of the lumen, the tent, over time, stretching the wall of the lumen and the blunt edge eroding the wall of the lumen at a point of contact, fibrotic tissue forming about the loop to secure the loop with respect to the wall of the lumen.

22. The method of claim 21 wherein the collapsible anchor has additional protrusions attached thereto, each additional protrusion having a loop, and further including:

allowing the loops of at least some of the additional protrusions to penetrate a wall of the lumen.

23. The method of claim 21 wherein deploying the collapsible anchor includes allowing the protrusion to bend away from the collapsible anchor to an angle of between 45 degrees and 135 degrees.

24. The method of claim 21 wherein deploying the collapsible anchor includes allowing the protrusion to bend away from the collapsible anchor to an angle of 80 degrees.

25. The method of claim 21 wherein penetrating the wall of the lumen with the loop includes engaging the wall with the edge of the loop.

26. The method of claim 21 wherein the protrusion includes a straight neck that connects the loop to the collapsible anchor, and further including:

bending the protrusion alongside the collapsible anchor to place the implant in a collapsed state; and inserting the implant, in the collapsed state, into the lumen.

27. The method of claim 21 wherein the protrusion includes wire formed in a helix that connects the loop to the collapsible anchor, and further including:

inserting the helix, in a collapsed state, into the lumen; and
releasing the helix from the collapsed state.

28. The method of claim 27 wherein penetrating the wall of the lumen further includes allowing fibrotic tissue to grow between coils in the helix.

29. The method of claim 27 further including:

collapsing the helix with a drawstring to disengage the helix from the tissue; and withdrawing the collapsible anchor from the lumen.

30. The method of claim 29 wherein collapsing the helix further includes shearing fibrotic tissue with coils of the helix.

31. The method of claim 21 wherein penetrating the wall of the lumen with the loop includes engaging the wall with a face of the loop.

32. The method of claim 21 wherein penetrating the wall of the lumen with the loop includes engaging the wall with an end effect at a tip of the loop.

33. The method of claim 21 further including:

extending an unsupported, thin-walled sleeve coupled to the collapsible anchor into the lumen.

34. The implant of claim 16, wherein the drawstring runs through either the opening in the loop or an additional retaining loop connected to the protrusion.

35. The implant of claim 29, wherein the drawstring runs through either the opening in the loop or an additional retaining loop connected to the protrusion.

36. The method of claim 21, wherein fibrotic tissue forms about and through the loop in a range of 2-4 weeks.

* * * * *